United States Patent [19]

Dias

[11] Patent Number: 5,217,018
[45] Date of Patent: Jun. 8, 1993

[54] ACOUSTIC TRANSMISSION THROUGH CLADDED CORE WAVEGUIDE

[75] Inventor: J. Fleming Dias, Palo Alto, Calif.

[73] Assignee: Hewlett-Packard Company, Palo Alto, Calif.

[21] Appl. No.: 352,517

[22] Filed: May 16, 1989

[51] Int. Cl.$^5$ .............................................. A61B 8/12
[52] U.S. Cl. ............................ 128/662.06; 333/154
[58] Field of Search .............. 128/661.08–661.10, 128/662.04–662.06; 333/149, 150, 154, 254; 385/7, 13, 40, 88

[56] References Cited

U.S. PATENT DOCUMENTS

| | | | |
|---|---|---|---|
| 3,654,574 | 4/1972 | Dias | 333/30 |
| 4,063,198 | 12/1977 | Wagers et al. | 333/30 |
| 4,743,870 | 5/1988 | Jen et al. | 333/147 |

FOREIGN PATENT DOCUMENTS 0083973  6/1983  European Pat. Off. .
WO87/01269  2/1986  PCT Int'l Appl. .

OTHER PUBLICATIONS

Jen, C. K., "Acoustic Fibers", 1987 Ultrasonics Symposium, vol. 1, Oct. 14–16, 1987, Sheraton Denver Tech Center, Denver, Colo., pp. 443–454.

*Primary Examiner*—Francis Jaworski

[57] ABSTRACT

An Ultrasonic Catheter Guidance System which overcomes the inadequacies, dangers, and difficulties encountered by previously available medical guiding apparatus is disclosed. The present invention utilizes a novel technique for coupling ultrasonic energy into an optical fiber that can be used within a blood vessel of patient's body. The present invention includes a transducer [44] which is precisely located on a thin slab of piezoelectric material [10] that generates ultrasonic acoustic surface waves [62] that propagate on the surface [13] or within the bulk of the slab [10]. The transducer [44] may be selected from a set of the many novel alternative configurations that are disclosed in the specification and illustrated by the drawings. The operating power and frequency of the present invention can be predetermined by altering the configuration of the transducers [44]. One or more optical fibers [32] are affixed to the thin slab [10] to ensure the maximum transfer of acoustic energy into the optical fibers [32]. Any number of transducers [44] may be assembled to form an array of transducers [70, 80] that can provide customized input of sound waves to one or more fibers [32]. The present invention also includes a novel acoustic window [93] formed at the remote end of the optical fiber [32]. These acoustic windows [93] facilitate precise directional control and efficient transmission of energy from the end of the fiber which will be situated within the patient. The Ultrasonic Catheter Guidance System described and claimed in this patent application provides a powerful tool which will enable surgeons and medical technicians to place a catheter inside the body with great accuracy. This invention will enable physicians to recognize infirmities, to treat illnesses, and to perform risk-free surgery with previously unavailable precision and effectiveness. The Ultrasonic Catheter Guidance System constitutes an important step forward for the medical profession.

10 Claims, 6 Drawing Sheets

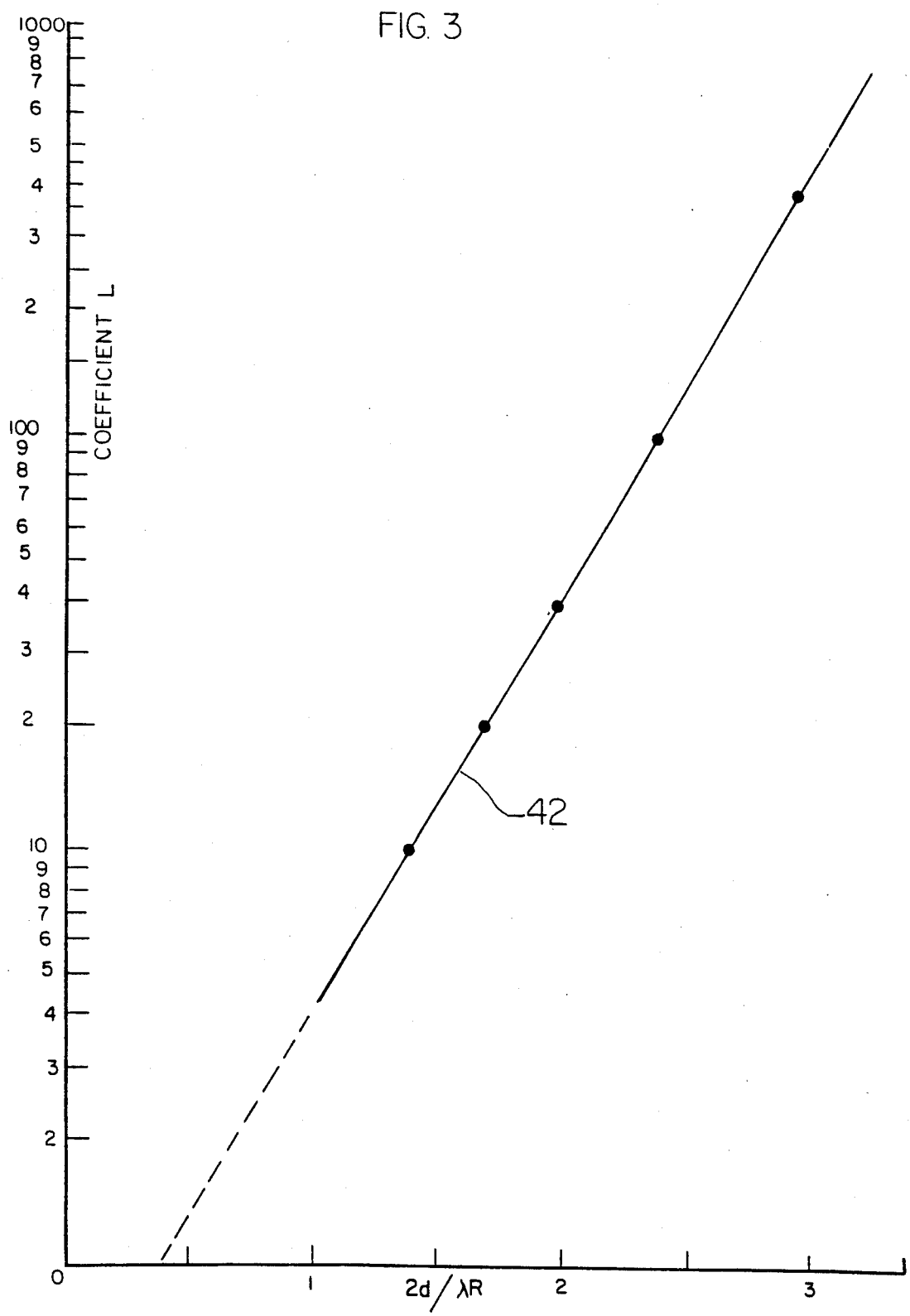

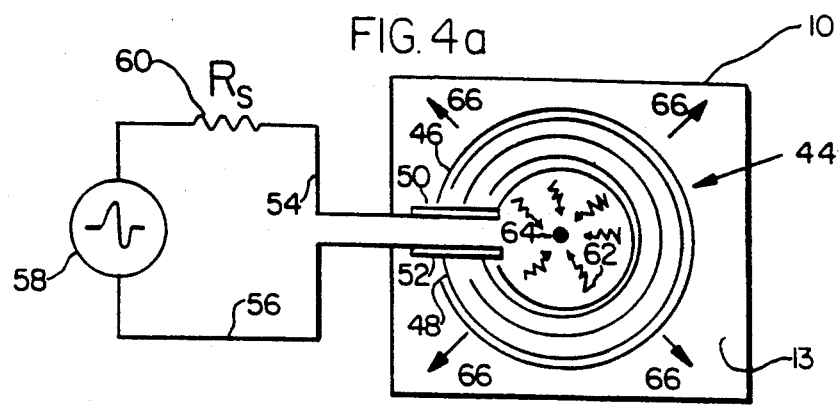
FIG. 4a
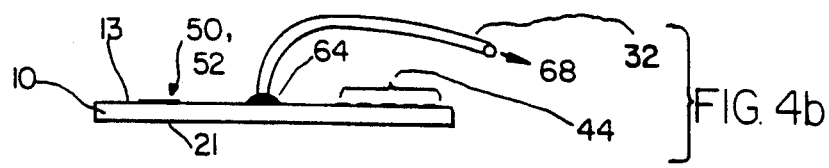
FIG. 4b
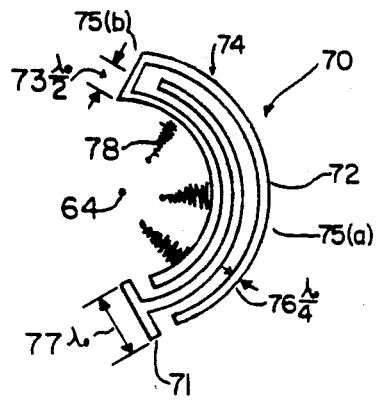
FIG. 5
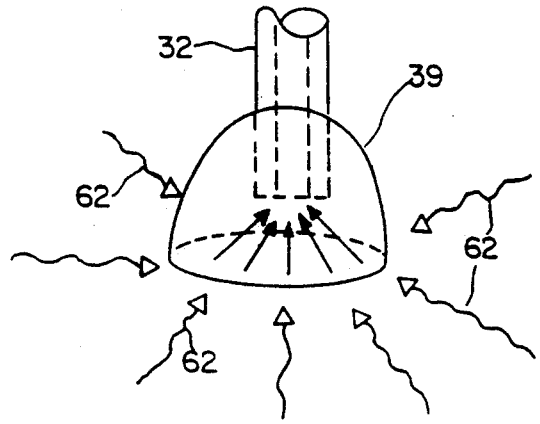
FIG. 6
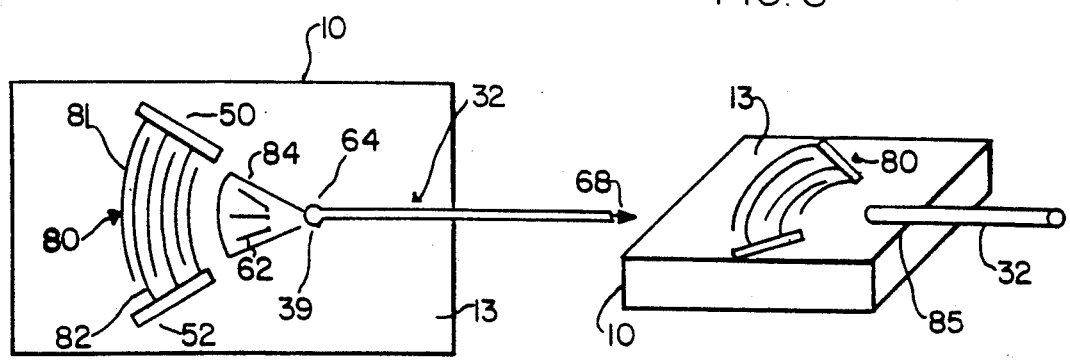
FIG. 7
FIG. 8

ACOUSTIC TRANSMISSION THROUGH CLADDED CORE WAVEGUIDE

BACKGROUND OF THE INVENTION

The present invention is a method and apparatus for the sonographic guidance and visualization of a catheter tip. The present invention includes both a device which is capable of coupling acoustic energy into optical fibers and a novel method of localizing the distal end of those fibers.

During a surgical operation, it may be necessary to insert a catheter or needle into a patient to perform a biopsy or to provide aspiration or drainage. The surgeon must know the exact location of this probe within the body. The visualization of the probe location is accomplished by directing ultrasonic energy into the patient and then by detecting the ultrasound reflections that bounce off of the catheter or needle. Over the past few decades, surgeons have relied upon the echogenic characteristics of the materials used to fabricate catheters and surgical needles to visualize the location of such a probe in the body or in a blood vessel. The echogenecity of a needle may be enhanced by roughening the outer surface of the needle or by applying a suitable coating. The reflectivity of these probes may also be improved by decreasing their diameter or by injecting air or water through their centers. These methods of achieving better echogenecity, however, are accompanied by serious limitations. As an example, scoring a needle does optimize its ability to produce ultrasound echoes, but the scoring also reduces the needle's strength.

Other previous attempts to enhance the surgeon's ability to visualize the tip of a probe or needle within the patient have included the use of an active device placed at the tip of the catheter. This modified catheter encloses a metal wire which conducts electrical energy from an outside source to its remote or distal end inside the body. The remote end of the catheter has an active ultrasonic transducer attached to its tip that emits acoustic energy. This energy is received by a sensor placed on the skin of the patient. This type of apparatus has also been used to detect the position of a metal needle which serves as a location reference after it has been inserted into a patient during a surgical operation. This catheter can be dangerous, however, because it carries electricity into the body. Many internal organs, including the heart and the brain, can be damaged by stray electrical currents. Another unattractive characteristic of this device is its high cost. Since each catheter and the complicated electronic transducer which it contains are used only once and are then discarded, this device is very expensive to use.

The problem of providing an accurate and reliable method of catheter visualization that avoids the danger of introducing stray electrical currents into the body has presented a major challenge to designers in the field of medical imaging. The development of a method and an apparatus that determines the precise location of such an instrument within the body would constitute a major technological advance. The enhanced performance that could be achieved using such an innovative system would satisfy a long felt need within the medical profession and would enable physicians to better care for their patients.

SUMMARY OF THE INVENTION

An ultrasonic catheter guidance system overcomes the inadequacies, dangers, and difficulties encountered by previously available medical guiding apparatus. The present invention utilizes a novel technique for coupling ultrasonic energy into an optical fiber that can be used within a blood vessel of patient's body. Although the optical fiber would normally be used to transport light from one place to another, it is extremely well suited for this novel combination. The optical fiber is safe to use, because it delivers acoustic energy directly into the body without metal wires that can carry dangerous electrical currents perilously close to sensitive organs like the heart and the brain. Since the optical fiber does not require complex transducers to convert electricity to sound waves inside the body, it is readily disposable and exceedingly cost-effective. The optical fiber conveys high intensity ultrasound to the exact location within the patient and locates the position of the catheter tip where the delivery of the sonic energy can be precisely controlled. An imaging probe placed outside on the body detects the tip position by conventional imaging procedures.

The present invention includes a transducer which is precisely located on a thin slab of piezoelectric material that generates ultrasonic acoustic surface waves that propagate on the surface or within the bulk of the slab. The transducer may be selected from a set of the many novel alternative configurations that are disclosed below and illustrated by the drawings. The operating power and frequency of the imager can be predetermined by altering the configuration of the transducers. One or more optical fibers are affixed to the thin slab to ensure the maximum transfer of acoustic energy into the optical fibers. Any number of transducers may be assembled to form an array of transducers that can provide customized input of sound waves to one or more fibers. The present invention also includes a novel acoustic window formed at the remote end of the optical fiber. These acoustic windows facilitate precise directional control and efficient transmission of energy from the end of the fiber which will be situated within the patient. The windows may be arranged in several novel and useful configurations which are presented below.

The novel ultrasound guiding methods claimed below utilize the apparatus that is made possible by the inventor's development of an effective interface that combines the safety of a passive ultrasound source with the intensity of an active source. By eliminating the placement of complex, costly, and potentially dangerous electrical mechanisms inside a patient and by using several of the ultrasound guiding structures described below, devices can be developed for the intravascular visualization of the extent of stenosis on the interior wall of blood vessels.

The ultrasonic catheter guidance system described and claimed in this patent application provides a powerful tool which will enable surgeons and medical technicians to place a catheter inside the body with great accuracy. This invention will enable physicians to recognize infirmities, to treat illnesses, and to perform risk-free surgery with previously unavailable precision and effectiveness. The ultrasonic catheter guidance system constitutes an important step forward for the medical profession.

An appreciation of other aims and objectives of the present invention and a more complete and comprehensive understanding of this invention may be achieved by studying the following description of a preferred embodiment and by referring to the accompanying drawings.

BRIEF DESCRIPTION OF THE DRAWINGS

FIG. 3 is a graph that exhibits the relationship between L, d, and $\lambda_R$. These three parameters dictate the optimal configuration of the slab and the transducer which ensures the greatest transfer of energy into the fiber at a given center frequency.

FIG. 4(a) is a top view of a slab bearing a multi-conductor interdigital transducer connected to a signal generator. FIG. 4(b) is a side view of the same slab which has been joined to an optical fiber.

FIG. 5 is a top view of an arcuate metallized stripe interdigital transducer.

FIG. 6 is a detailed view of the epoxy bond that binds the optical fiber to the slab.

FIG. 7 is a top view of an optical fiber coupled to a slab at the focus point of an arcuate transducer which includes radial electrodes.

FIG. 8 is a perspective view of an alternative embodiment of the invention which reveals the optical fiber seated in a groove formed in the slab.

DETAILED DESCRIPTION OF THE PREFERRED EMBODIMENTS

The Apparatus

Figure 1A:
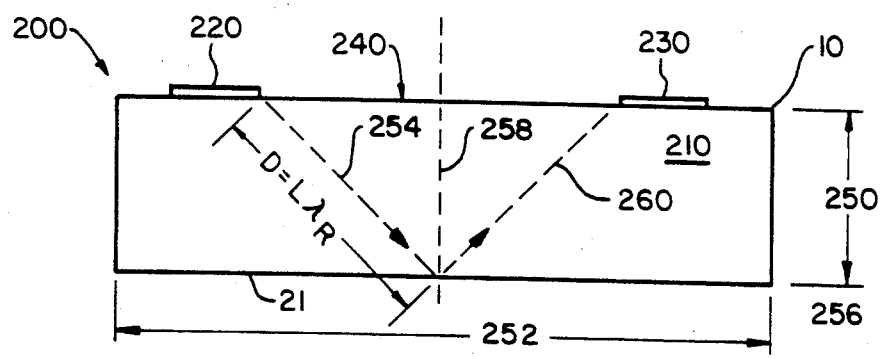
FIGS. 1(a) and 1(b) are diagrams revealing a cross-section and a top view of a slab of piezoelectric material which is capable of conducting acoustic energy. These figures illustrate the propagation of ultrasound waves from a transducer into the slab.
Figure 1B:
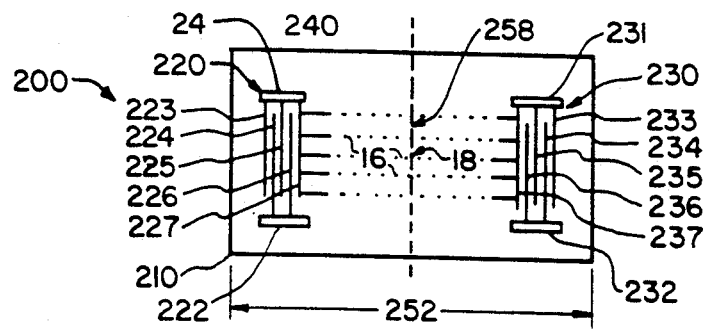

As shown in FIGS. 1(a) and 1(b), a transducer 200 includes a piezoelectric substrate 210, a first interdigitated electrode pair 220 and a second interdigitated electrode pair 230. Electrode pair 220 includes a first electrode 221 and a second electrode 222. First electrode 221 includes electrode segments 223, 225 and 227. Second electrode 222 includes electrode segments 224 and 226. Electrode segments 223-227 are parallel to each other. Likewise, electrode pair 230 includes electrodes 231 and 232. Electrode 231 includes electrode segments 233, 235 and 237, while electrode 232 includes electrode segments 234 and 236. Electrode segments 233-237 are parallel to each other. Both electrode pairs 220 and 230 are fabricated on a basal plane surface 240 of substrate 210. Piezoelectric substrate 210 is lead zirconium titanate (PZT). The thickness 250 and width 252 of substrate 210 are determined by relationships that have been derived from the principles of acoustic wave theory, which are presented in detail below.

When electrode pair 220 is energized by a remote signal generator (not shown), waves of ultrasound 254, exceeding a frequency of one megahertz (1 MHz), emanate from first electrode pair 220 and reflect of a bottom surface 256 of substrate 210 at a point which lies on a vertical plane 258. The reflective waves 260 traverse substrate 210 and arrive at basal plane surface 240 at the location of second electrode pair 230.

Figure 2A:
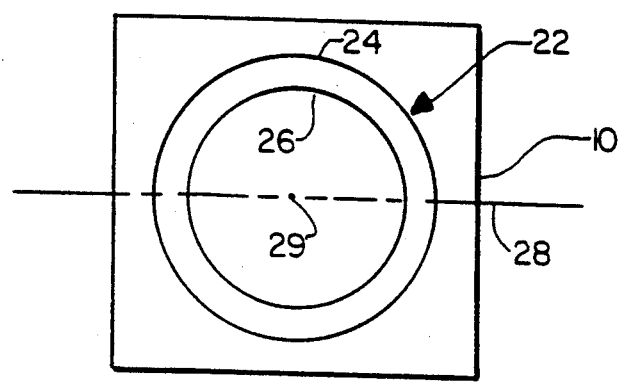
FIG. 2(a) is a top view of a slab like the one shown in FIG. 1(a).
Figure 2B:
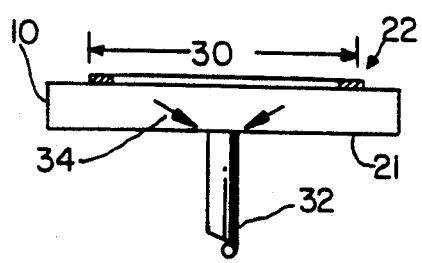
FIGS. 2(b) and 2(c) are side views of two embodiments of the invention which reveal two configurations for coupling acoustic energy into an optical fiber.
Figure 2C:
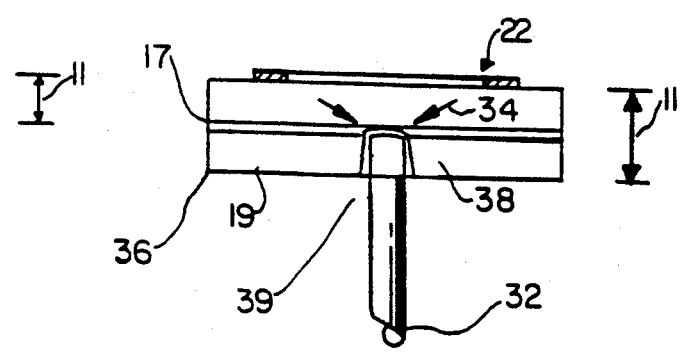

FIG. 2(a) presents a top view of a slab 10 like the one shown in FIGS. 1(a) and 1(b). A circular interdigital transducer 22 comprises a pair of circular conductors 24 and 26 which focus acoustic energy on focus point 29, which lies on vertical axis 18. FIG. 2(b) is a side view of the slab 10 shown in FIG. 2(a). The circular interdigital transducer 22, which has a separation between the two conductors 24 and 26 indicated by the reference numeral 30, is positioned on the top surface 13 of the slab 10 so that an optical fiber 32 receives the greatest possible amount of ultrasonic energy 34. The multimode optical fiber 32 is capable of conducting ultrasound above the one megahertz (MHz) frequency range, and is particularly effective at frequencies between twenty and forty megahertz. The optical fiber 32 is joined to the slab 10 over focus point 29. In FIG. 2(c), the optical fiber 32 has been connected to a double-width slab 36 by seating it in a laser-drilled recess 38 filled with an epoxy material 39. A layer of glue 17 holds a slab of low acoustic impedance material 19 to the upper PZT slab 10. The purpose of the lower slab 19 is to provide rigidity to the PZT.

The optimal configuration of the slab 10 and the transducer 22 is determined by the principles of acoustic theory. If the thickness 11 of the slab 10 is large, an acoustic wave generated by the transducer 22 will propagate along the top surface of the slab 10 as a Rayleigh wave or Surface Acoustic Wave (SAW) without penetrating below the surface. In the present context, term "large" refers to a thickness, t, that is greater than one hundred wavelengths of the selected frequency of acoustic energy. When the thickness of the slab is reduced to a few wavelengths, the sound waves degenerate into quasi-Rayleigh waves and enter the slab. As shown in FIG. 2, the sound waves 16 can be guided from transducer 22 through the slab 10 toward a focus point 29 where they can be directed into an optical fiber 32 mounted on the opposite face 21 of the slab 10. The waves traverse a distance, D, from the transducer to the focus point which is equal to the Rayleigh wavelength, $\lambda_R$, times a multiplier, L. The relationship between L, d, and $\lambda_R$ is presented in *Rayleigh and Lamb Waves* by I. A. Viktorov, published by Plenum Press in New York in 1967. A graph 42 that exhibits the dependence of L on the parameters d and $\lambda_R$ is shown in FIG. 3. Based upon the dimension 11 and the frequency of operation of the interdigital transducer, the value of L can be obtained from FIG. 3. In FIG. 2, 2D corresponds to the dimension 30. Because L changes exponentially with 2d, the thickness of the slab must be chosen to obtain a small value of L and consequently a small value for the dimension 30. If the transducer 22 operates at a center frequency of 20 MHz and if the Rayleigh wave velocity of the slab material is 2100 meters per second, then the Rayleigh wavelength can be computed using the following expression:

$$\lambda_R = \text{(Rayleigh wave velocity)/(transducer frequency)}$$
$$\lambda_R = 2100 * 10^3/20 * 10^6 = 0.105 \text{ mm}$$

If 10 mils is selected as the thickness of the slab, 2d=0.25 mm, it therefore follows that:

$$2d/\lambda_R = 0.25/0.105 = 2.38.$$

From the graph provided by FIG. 3, the value 2.38 along the x-axis corresponds to a value of about 100 along the abscissa. Since $D = L*\lambda_R$, the desired distance, D, for these conditions is $100*0.105 = 10.5$ mm. For a transducer frequency of 40 MHz, the same arithmetic yields a value of D=5.25 mm. The important consequence of this analysis is that many different transducers having different diameters and operating at different frequencies may be fabricated on the same slab or substrate.

FIG. 4(a) supplies a top view of a slab 10 bearing a multi-conductor interdigital transducer 44 which includes first and second polarity conductor rings 46 and 48 connected to first and second polarity electrodes 50 and 52. Transducer 44 is connected by first and second polarity leads 54 and 56 to a signal generator 58 through resistor 60. This resistor represents the source impedance of the signal generator. Ultrasound waves 62 are shown emanating from transducer 44 to a focal point 64 at the center of the conductor rings 46 and 48. Some energy 66 is wasted and fans out across the basal plane surface 13 of the slab 10. Using suitable attenuating material on surface 13, this energy could be absorbed. A more efficient transducer can be constructed by making the transducer unidirectional. FIG. 4(b) is a side view of the same slab 10 which has been joined to an optical fiber 32 on the same side of the slab that bears the transducer 44. The thickness of slab 10 is greater than 50$\lambda$ and therefore the acoustic surface wave will propagate on the top surface and come to a focus at 64. The junction at focal point 64 permits the largest share of acoustic energy 68 to be coupled into the fiber 32 and travel toward the fiber's distant end to a location within a patient's body (shown in FIGS. 18, 19, and 20).

FIG. 5 is a top view of a curved or arcuate metallized stripe interdigital transducer 70, which directs energy to focal point 64. This transducer 70 may serve as an alternative to the transducer 44 shown in FIG. 4(a). The metallized stripes are vacuum deposited on the slab 10 using conventional photolithographic techniques well known to those persons ordinarily skilled in integrated circuit fabrication arts. Generally a one hundred Angstrom base layer of chromium and a top layer of gold three thousand Angstroms thick are employed. In an alternative embodiment, a base layer of titanium is used and a top layer of aluminum or gold is used. The thickness of the top layer may be increased to fabricate higher power transducers. Transducer 70 includes an electrode 71, a central arcuate conductor 72, and an outer conductor pair 74. Reference numeral 73 indicates the separation distance between successive conductors of dissimilar polarity. The outer arcuate conductor pair 74 includes two concentric partial ring segments 75a and are joined by a connector portion 75b. In the preferred embodimentm this connector 75b is orthogonal to the conductor pair 74. Each metallized stripe which is formed into an arcuate conductor has a width denoted by dimension 76. The separation distance between arcuate conductors of similar polarity is indicated by dimension 77. The outer conductor pair 74 is grounded by connection 78. The dimensions given by reference numerals 73, 76, and 77 are all based upon the value of $\lambda_o$ ($\lambda_o = \lambda_f$). This wavelength can be determined by employing the following function:

$$\lambda_f = V_f/f_o$$

where $V_f$ is the surface velocity of the ultrasonic waves. Both the power level of the transducers and their operating frequencies can be changed by altering the thickness and spacing of the metal stripes. In general, all of the transducers 12, 22, 44, and 70 described in this application can be fabricated using planar technology. The stripes or traces are alternately connected to the electrode pads as shown. An electrical excitation signal is applied to the pads to produce ultrasonic energy. The present invention may utilize an interdigital transducer having any number of conductor pairs. The bandwidth of the transducer is inversely proportional to the number of conductor pairs.

The designer of the transducer decides on the frequency $f_o$ for a particular application. The value for the surface acoustic wave velocity $V_f$ is known. Using the formula noted above, a value for $\lambda_f$ can be determined. The photolithographic mask is then made using this value. If any other frequency is chosen, the value of $\lambda_f$ will be different because $V_f$ is a constant value. Consequently, the spacing of the conductive fingers on the mask and the final product will correspond to the new value of $\lambda_f$. Any operating frequency can be chosen and the corresponding values of $\lambda_f$ obtained to fabricate transducers operating at those frequencies. Although this statement is generally accurate, the use of piezoelectric material imposes some limitations. PZT, for example, can be employed for frequencies up to 120 MHz. Beyond that level, the losses increase and the transducer becomes inefficient. Improvements can be obtained by depositing zinc oxide films on a polished surface of fused quartz over the areas where the transducers have been deposited. This additional step reduces surface losses and increases the highest value of the frequency of operation.

FIG. 6 shows an enlarged view of the epoxy bond 39 that binds the optical fiber 32 to the slab 10. Energy enters the bead of epoxy 39 at an angle dictated by the ratio of the velocities of the sound waves on the surface of the slab and in the epoxy. The angle is given by the expression:

$$\sin^{-1}\theta = V_e/V_f$$

where $V_e$ is the speed through the epoxy material. The coupling material that is use has a longitudinal velocity that is less than the surface wave velocity on the piezoelectric slab on which the wave is propagated. Commercially available substances such as buthyl rubber, RTV, and Sylgard elastomer can be used. An alternate material could be an indium-tin low temperature solder. If a small diameter bead is used, then the height of the bead above the slab must be increased.

FIG. 7 is a top view of an optical fiber 32 coupled to a slab 10 using an epoxy bond 39 at the focus point 64 of an arcuate array transducer 80 which includes radial electrodes 50 and 52. Arcuate conductor segments 81 and 82 are each coupled in an alternating arrangement to electrodes 50 and 52. In general, all of the transducers 12, 14, 22, 44, 70, and 80 described in this patent application can be fabricated using well-known planar technology and can be attached to either side of the PZT substrate 10.

FIG. 8 presents a perspective view of an alternative embodiment of the invention which reveals the optical fiber 32 seated in a tapered guide or groove 85 formed in the slab 10. This groove is cut to a depth of less than one-half the Rayleigh wavelength. As an alternative, the fiber could also be butted against the edge of the slab and epoxied in place.

Figure 9:
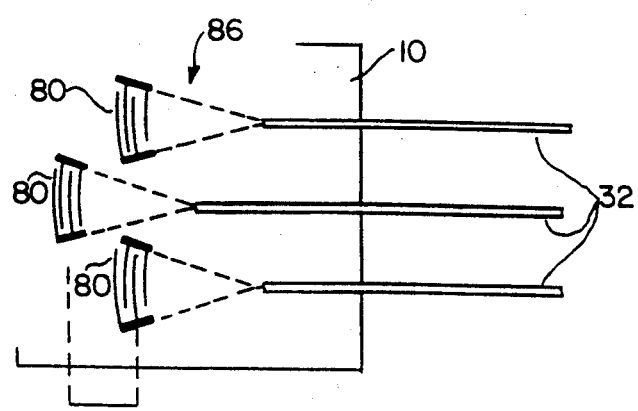
FIG. 9 depicts a top view of a multi-transducer array formed on a single slab with corresponding grooves at their foci.

FIG. 9 depicts a top view of a multi-transducer array 86 formed on a single slab 10.

Figure 11:
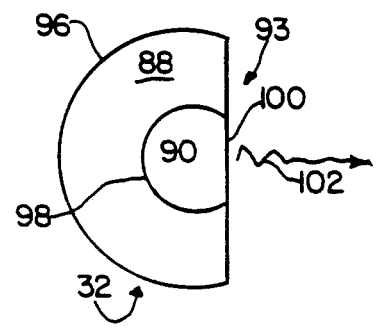
FIG. 11 is a cross-sectional view looking down the end of the fiber shown in FIG. 10.
Figure 10:
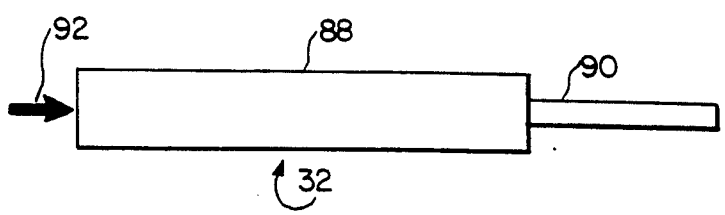
FIG. 10 is a side view of a modified optical fiber showing both the core and cladding portions of the fiber.
Figure 14:
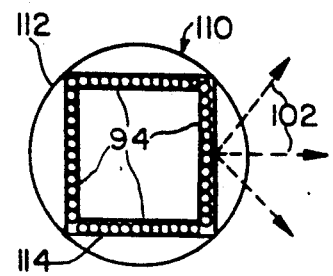
FIG. 14 is a cross-sectional illustration of a rectangular array of acoustic windows.
Figure 12:
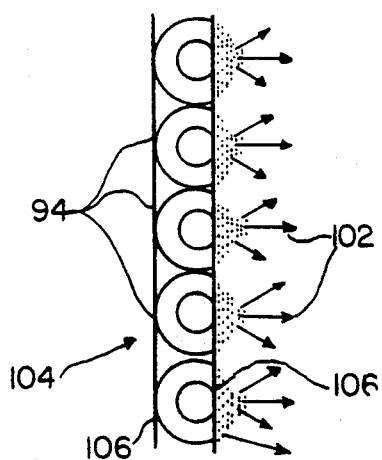
FIG. 12 is a partial cross-sectional view of a linear array of acoustic windows.
Figure 13:
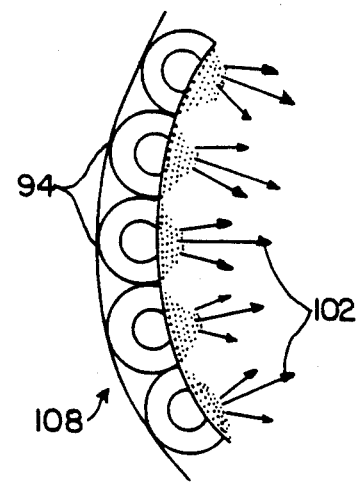
FIG. 13 is a partial cross-sectional view of a curved array of acoustic windows.

FIG. 10 is a side view of an optical fiber 32 showing both the cladding 88 and core 90 portions of the fiber 32. Ultrasonic energy 92 entering the proximal end of the fiber 32 propagates down the fiber by total internal reflection at the core-cladding interface. The difference between the refractive indices of the cladding and the core is very small and, as a consequence, a portion of the energy that propagates through this guide leaks into the cladding. A small portion of the cladding 88 can be removed from the core 90 to form a window or exit for the acoustic energy at the distal end of the fiber. This removal of a portion of the cladding 88 results in the dispersion of ultrasound in all directions. FIG. 11 provides a cross-sectional view looking down the distal end of a fiber 32. This cross-section reveals an end face 93, an outside diameter 96 of the cladding 88, an outside diameter 98 of the fiber core 90, and a transverse cut or lapped portion 100. The input energy 92 which enters the fiber 32 at its proximal end near the transducer leaves the fiber as output energy 102 through the transverse cut 100. This cut, which is also called a slit window, can be used to precisely control the direction of the radiating ultrasound from the distal end of the fiber. The device pictured in FIG. 11 can be referred to as an "acoustic window" 94 which directs ultrasound into the patient. FIG. 12 presents a partial cross-sectional view of a linear array 104 of acoustic windows 94 contained by parallel array walls 106. FIG. 13 supplies a partial cross-sectional view of a curved array 108 of acoustic windows 94. Another alternative embodiment of an array of acoustic windows 94 is shown in the cross-sectional illustration of a rectangular array 114 enclosed by a catheter 112 portrayed by FIG. 14. Since the diameter of these fibers is relatively small, many can be fitted within the inside diameter of a 2 to 3 mm catheter 112. By phasing the excitation pulses at the transducers, the sonic energy can be focused and the resulting beam can be scanned as in a phased array. The curved array 108 provides a built-in means of pre-focusing.

The Guiding Methods and Systems

I. Previous techniques.

Figure 15A:
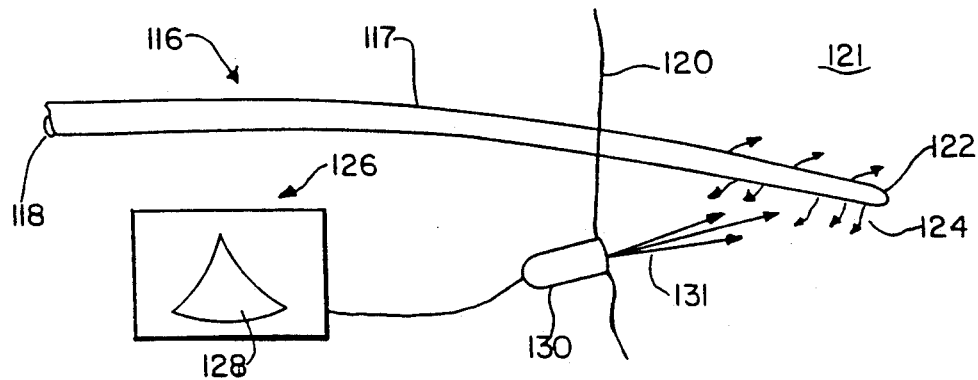
FIGS. 15a and 15b are a schematic renderings of a previous passive imaging systems which employs an interrogating beam.
Figure 15B:
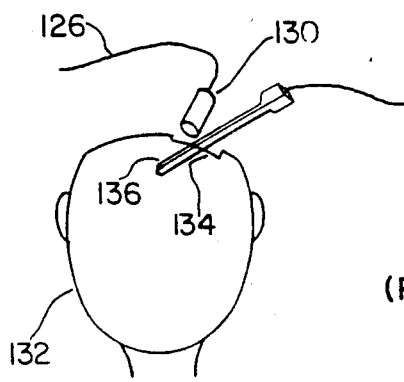

FIG. 15(a) presents a schematic rendering of a previous passive guiding system 116 which employs an interrogating beam. A passive catheter 117 has been inserted into a patient's body within a large artery. The distal end 118 of catheter 117 reflects ultrasound that impinges upon its echogenic distal end 122. The reflected ultrasound 124 is sensed by a detector 130 which is coupled to an analyzer 126 that interprets the gathered reflections and produces an image on a display screen 128. The detector 130 also emits an interrogating beam 131 which helps to locate the distal end 122 of the catheter 117. FIG. 15(b) shows how this same conventional technique has been practiced in the course of surgical operations on the brain. The surgeon has bored a hole 134 in the skull of a patient 132 and has inserted a needle or other surgical tool 136 into the brain. The position of the needle 136 is determined by irradiating the patient with waves from detector 130.

Figure 16:
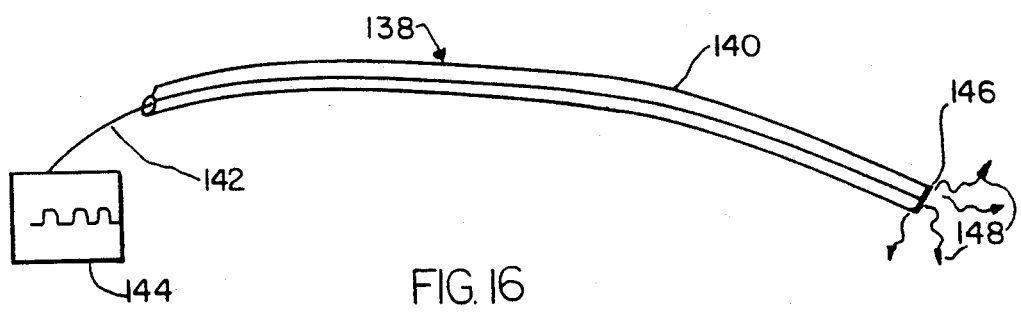
FIG. 16 is a schematic depiction of a previous active imaging system that uses an electrode at the distal end of a catheter to irradiate a body.

FIG. 16 is a schematic depiction of a second previous guiding system 138 that uses an ultrasound source at the distal end of a catheter to irradiate sound through the body. Unlike the passive system 116 described in the previous paragraph, FIG. 16 presents an active system 138 which includes a catheter 140 that encloses an electrical wire 142 which, in turn, is coupled to a pulser 144. A piezoelectric element 146 affixed to the distal end of the catheter 140 is energized by the pulser 144 and converts an electrical current to sound waves 148 which travel through the body, are sensed by a detector 130, and are displayed on the screen of a conventional imaging system.

Figure 17:
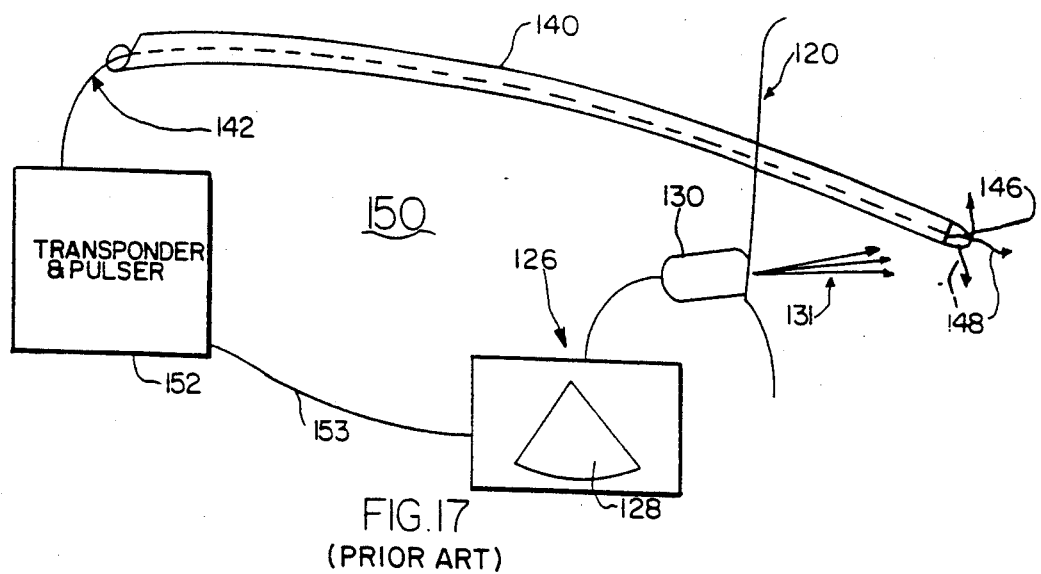
FIG. 17 is a schematic diagram of a previous transponder and pulser imaging system.

A third previous guiding system 150 is displayed in schematic form in FIG. 17. This conventional system 150 incorporates a piezoelectric transducer 146 located at the distal end of a catheter 140. The transducer is connected to a pulser through a transponder 152. When the guiding probe 130 emits ultrasound in the general direction of the transducer 146, the transducer is stimulated by the sound energy that it receives and begins to emit a small electrical signal through wire 142 to the transponder 152. The transponder activates the pulser when it receives these small electrical signals and, in turn, sends large amplitude pulses to transducer 146. Transducer 146 then emits sound pulses 148 through the body to the imaging transducer 130. The display 128 of the imaging systems 126 then shows the unambiguous location of the catheter tip in relation to the anatomical features that are being imaged by the ultrasound.

Each of these three conventional guiding systems 116, 138, and 150 suffers from the various shortcomings and drawbacks that are described above in the background section. They are described and depicted here only to emphasize the substantial differences between these prior guiding techniques and the methods of the present invention which are disclosed in detail and claimed below.

II. The Guiding System provided by the Present Invention

Figure 18:
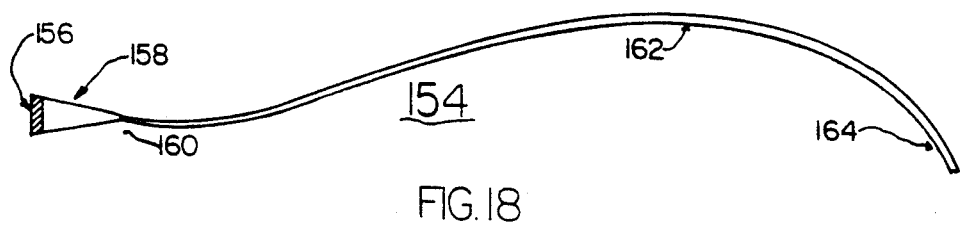
FIG. 18 presents an illustration of the present invention which reveals an ultrasound transducer coupled to an optical fiber.

FIG. 18 is an illustration of the present invention which reveals an guiding system 154 including an ultrasound transducer 156 coupled to an optical fiber 162 through a conical coupling device 158 and an acoustic bond 160. The distal end of fiber 162 terminates in a cylindrical segment 164. This segment is obtained by heating the fiber end with a flame until the glass melts and the core and cladding become one material for the length of this segment.

Figure 19:
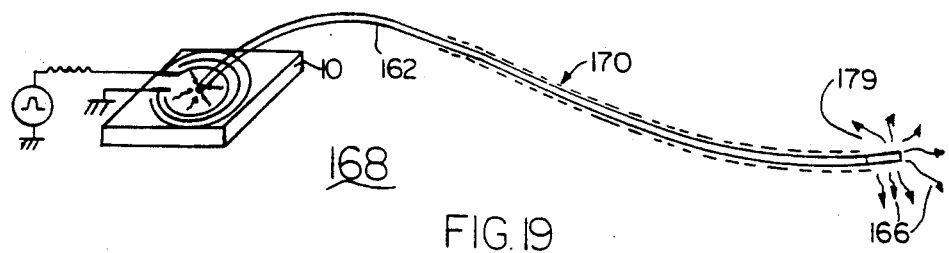
FIG. 19 exhibits the present invention in detail, revealing a bundle of optical fibers enclosed within a catheter and joined to a transducer through a coupling bead.
Figure 20A:
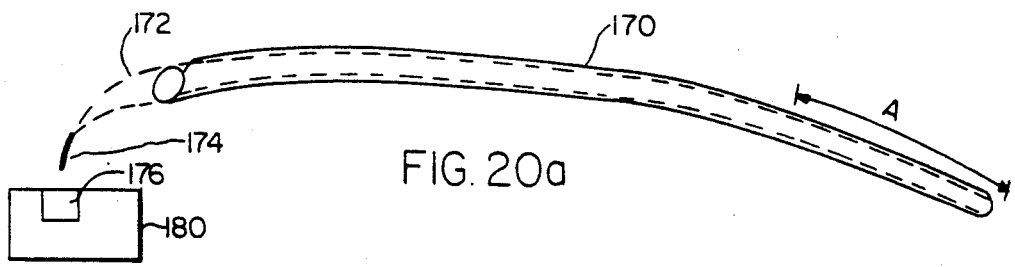
FIGS. 20(a) and (b) present side views of the present invention depicting the optical fiber with a portion of its core exposed.
Figure 20B:
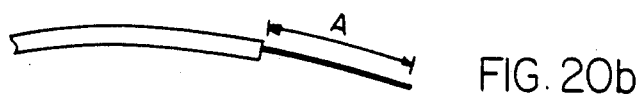

FIG. 19 exhibits the guiding system 168 of the present invention in detail, revealing an optical fiber 162 enclosed within a catheter 170. Ultrasound waves are emitted from the distal end 179 of the catheter 170. FIGS. 20(a) and (b) present side views of the present invention depicting an optical fiber bundle 172 within a catheter 170. The fibers are coupled at their proximal end at a joint 174. Joint 174 is attached to a transducer 180 that includes a coupling fluid 176. In the preferred embodiment, joint 174 serves as a quick connect and disconnect coupler. A portion of the fiber core is exposed at the fiber's distal end.

The Ultrasonic Catheter Guidance System disclosed and claimed in this application provides an accurate and powerful tool for a wide variety of medical applications. This invention constitutes a major step forward in the continually evolving field of medical imaging.

Although the present invention has been described in detail with reference to a particualr preferred embodiment, persons possessing ordinary skill in the art to which this invention pertains will appreciate that various modifications and enhancements may be made without departing from the spirit and scope of the claims that follow.

What is claimed is:

1. An acoustic system comprising:
   an acoustic waveguide comprising a longitudinally extending core and a longitudinally extending cladding about said core;
   a transducer, said transducer having a piezoelectric substrate with opposing first and second surfaces, said transducer having a first electrode and a second electrode on said first surface;
   a signal generator for applying an alternating voltage differential between said electrodes; and
   coupling means for acoustically coupling said transducer with said acoustic waveguide.

2. An acoustic system as recited in claim 1 wherein said transducer is configured to generate quasi-Rayleigh waves that penetrate obliquely into said substrate, and wherein said coupling means physically attaches said acoustic waveguide to said second surface.

3. An acoustic system as recited in claim 1 wherein said coupling means includes a fluid through which said acoustic wavefront is coupled from said first surface to said acoustic waveguide.

4. An acoustic system as recited in claim 1 wherein said first electrode includes a first electrode segment and said second electrode includes a second electrode segment substantially parallel to said first electrode segment.

5. An acoustic system as recited in claim 4 wherein said first electrode segment and said second electrode segment are arcuate.

6. An acoustic system as recited in claim 1 wherein said acoustic waveguide has a proximal end and a distal end.

7. An acoustic system as recited in claim 6 wherein said coupling means couples said transducer to said acoustic waveguide so that acoustic energy from said transducer enters said acoustic waveguide through said proximal end.

8. An acoustic system as recited in claim 6 further comprising an acoustic detector arranged remotely from said distal end so as to be able to detect acoustic energy emanating therefrom, whereby the location of said distal end can be determined from the output of said detector.

9. A method of coupling acoustic energy into an acoustic waveguide having a core and a cladding about said core, said method comprising the steps of:
   generating an alternating voltage differential;
   applying said alternating voltage differential to a pair of electrodes on the surface of a piezoelectric substrate so as to generate acoustic energy in the form quasi-Rayleigh waves that transmit obliquely through said substrate; and
   coupling said acoustic energy into said acoustic waveguide so that it takes the form of longitudinal acoustic waves within said acoustic waveguide.

10. A method as recited in claim 9 further comprising:
   conveying said acoustic energy to a distal end of said acoustic waveguide so that it is transmitted into a body therefrom;
   detecting said acoustic energy using a detector outside said body; and
   determining from said detection the location of said distal end.

* * * * *